US008834931B2

(12) United States Patent
Bilgic

(10) Patent No.: US 8,834,931 B2
(45) Date of Patent: Sep. 16, 2014

(54) DRY POWDER FORMULATION CONTAINING TIOTROPIUM FOR INHALATION

(75) Inventor: Mahmut Bilgic, Istanbul (TR)

(73) Assignee: Mahmut Bilgic, Istanbul (TR)

( * ) Notice: Subject to any disclaimer, the term of this patent is extended or adjusted under 35 U.S.C. 154(b) by 0 days.

(21) Appl. No.: 13/531,972

(22) Filed: Jun. 25, 2012

(65) Prior Publication Data

US 2013/0017257 A1 Jan. 17, 2013

Related U.S. Application Data

(63) Continuation-in-part of application No. PCT/TR2010/000185, filed on Sep. 22, 2010, and a continuation-in-part of application No. PCT/TR2010/000187, filed on Sep. 22, 2010, and a continuation-in-part of application No. PCT/TR2010/000188, filed on Sep. 22, 2010, and a continuation-in-part of application No. PCT/TR2010/000189, filed on Sep. 22, 2010, and a continuation-in-part of application No. PCT/TR2010/000251, filed on Dec. 20, 2010, and a continuation-in-part of application No. PCT/TR2011/000011, filed on Jan. 28, 2011, and a continuation-in-part of application No. PCT/TR2011/000012, filed on Jan. 28, 2011, and a continuation-in-part of application No. PCT/TR2011/000014, filed on Jan. 28, 2011, and a continuation-in-part of application No. PCT/TR2011/000015, filed on Jan. 28, 2011, and a continuation-in-part of application No. PCT/TR2011/000018, filed on Jan. 28, 2011, and a continuation-in-part of application No. PCT/TR2011/000019, filed on Jan. 28, 2011, and a continuation-in-part of application No. PCT/TR2011/000021, filed on Jan. 28, 2011, and a continuation-in-part of application No. PCT/TR2011/000022, filed on Jan. 28, 2011, and a continuation-in-part of application No. PCT/TR2011/000023, filed on Jan. 28, 2011.

(51) Int. Cl.
*A61K 9/14* (2006.01)
*A61K 31/46* (2006.01)
*A61K 9/00* (2006.01)

(52) U.S. Cl.
CPC ............... *A61K 9/0075* (2013.01); *A61K 31/46* (2013.01)
USPC ............................ 424/489; 424/400; 514/291

(58) Field of Classification Search
None
See application file for complete search history.

(56) References Cited

U.S. PATENT DOCUMENTS

| | | | | |
|---|---|---|---|---|
| 4,335,121 | A | 6/1982 | Phillipps et al. | |
| 6,475,467 | B1 | 11/2002 | Keller et al. | |
| 6,645,466 | B1 | 11/2003 | Keller et al. | |
| 7,070,800 | B2 | 7/2006 | Bechtold-Peters et al. | |
| 2002/0183292 | A1 | 12/2002 | Pairet et al. | |
| 2003/0018019 | A1 | 1/2003 | Meade et al. | |
| 2003/0064031 | A1 | 4/2003 | Humphrey et al. | |
| 2004/0009963 | A1 | 1/2004 | Horstman et al. | |
| 2004/0152720 | A1 | 8/2004 | Hartig et al. | |
| 2004/0226869 | A1 | 11/2004 | McClure et al. | |
| 2005/0121027 | A1 | 6/2005 | Nilsson et al. | |
| 2005/0123486 | A1 | 6/2005 | Nilsson et al. | |
| 2005/0196346 | A1 | 9/2005 | Bechtold-Peters et al. | |
| 2006/0039868 | A1 * | 2/2006 | Bechtold-Peters et al. | 424/45 |
| 2007/0212422 | A1 | 9/2007 | Keller et al. | |
| 2009/0088408 | A1 | 4/2009 | Meade et al. | |
| 2009/0188497 | A1 | 7/2009 | Nilsson et al. | |
| 2009/0311314 | A1 | 12/2009 | Hartig et al. | |

FOREIGN PATENT DOCUMENTS

| | | | |
|---|---|---|---|
| DE | 19835346 | A1 | 2/2000 |
| EP | 0418716 | A1 | 3/1991 |
| WO | WO-00/07567 | A1 | 2/2000 |
| WO | WO-00/47200 | A1 | 8/2000 |
| WO | WO-01/78739 | A1 | 10/2001 |
| WO | WO-01/78743 | A1 | 10/2001 |
| WO | WO-01/78745 | A1 | 10/2001 |
| WO | WO-02/36106 | A2 | 5/2002 |
| WO | WO-02/49616 | A1 | 6/2002 |
| WO | WO-03/000241 | A2 | 1/2003 |
| WO | WO-2004/019985 | A1 | 3/2004 |
| WO | WO-2004/110404 | A1 | 12/2004 |
| WO | WO-2005/044187 | A2 | 5/2005 |
| WO | WO-2005/053646 | A1 | 6/2005 |
| WO | WO-2005/053648 | A1 | 6/2005 |
| WO | WO-2006/086130 | A2 | 8/2006 |
| WO | WO-2008/021142 | A2 | 2/2008 |
| WO | WO-2008/102128 | A2 | 8/2008 |
| WO | WO-2009/007687 | A2 | 1/2009 |

(Continued)

OTHER PUBLICATIONS

SK Tee, C Marriott, XM Zeng, GP Martin. "The use of different sugars as fine and coarse carriers for aerosolised salbutamol sulphate." International Journal of Pharmaceutics, vol. 208, 2000, pp. 111-123.*

XM Zeng, KH Pandhal, GP Martin. "The influence of lactose carrier on the content homogeneity and dispersibility of beclomethasone dipropionate from dry powder aerosols." International Journal of Pharmaceutics, vol. 197, 2000, pp. 41-52.*

(Continued)

*Primary Examiner* — Frederick Krass
*Assistant Examiner* — Isaac Shomer
(74) *Attorney, Agent, or Firm* — Clark & Elbing LLP

(57) ABSTRACT

The present invention is related to a dry powder formulation containing tiotropium to be administered via inhalation, the use of said formulation in the treatment of respiratory diseases especially asthma and COPD (Chronic obstructive pulmonary disease), and the production process of said formulation.

37 Claims, No Drawings

(56) References Cited

FOREIGN PATENT DOCUMENTS

| WO | WO-2009/029028 A1 | 3/2009 |
|---|---|---|
| WO | WO-2010/007446 A1 | 1/2010 |
| WO | WO-2011/078818 A1 | 6/2011 |
| WO | WO-2011/093817 A1 | 8/2011 |

OTHER PUBLICATIONS

Cazzola et al., "A pilot study to assess the effects of combining fluticasone propionate/salmeterol and tiotropium on the airflow obstruction of patients with severe-to-very severe COPD," *Pulmonary Pharmacology & Therapeutics* 20:556-561, 2007.

Chow et al., "Investigation of electrostatic behavior of a lactose carrier for dry powder inhalers," *Pharmaceutical Research* 25:2822-2834, 2008.

James et al., "The surface characterization and comparison of two potential sub-micron, sugar bulking excipients for use in low-dose, suspension formulations in metered dose inhalers," *International Journal of Pharmaceutics* 361:209-221, 2008.

Pauwels, "The current place of nedocromil sodium in the treatment of asthma," *Journal of Allergy and Clinical Immunology* 98:S151-S156, 1996.

Search Report for Turkish Application No. 2009/09788, mailed Aug. 16, 2011 (16 pages).

Singh et al., "Superiority of 'triple' therapy with salmeterol/ fluticasone propionate and tiotropium bromide versus individual components in moderate to severe COPD," *Thorax* 63:592-598, 2008.

Van Noord et al., "The efficacy of tiotropium administered via Respimat® Soft Mist™ Inhaler or HandiHaler® in COPD patients," *Respiratory Medicine* 103:22-29, 2009.

Welte, "Optimising treatment for COPD—new strategies for combination therapy," *International Journal of Clinical Practice* 63:1136-1149, 2009.

Welte et al., "Efficacy and tolerability of budesonide/formoterol added to tiotropium in patients with chronic obstructive pulmonary disease," *American Journal of Respiratory and Critical Care Medicine* 180:741-750, 2009.

Written Opinion and International Search Report for PCT/TR2010/000185, mailed Dec. 22, 2010 (7 pages).

Written Opinion and International Search Report for PCT/TR2010/000187, mailed Nov. 15, 2010 (10 pages).

Written Opinion and International Search Report for PCT/TR2010/000188, mailed Dec. 22, 2010 (8 pages).

Written Opinion and International Search Report for PCT/TR2010/000189, mailed May 23, 2011 (9 pages).

Written Opinion and International Search Report for PCT/TR2010/000251, mailed May 11, 2011 (8 pages).

Written Opinion and International Search Report for PCT/TR2011/000011, mailed Dec. 28, 2011 (12 pages).

Written Opinion and International Search Report for PCT/TR2011/000012, mailed Dec. 28, 2011 (12 pages).

Written Opinion and International Search Report for PCT/TR2011/000014, mailed Dec. 21, 2011 (13 pages).

Written Opinion and International Search Report for PCT/TR2011/000015, mailed Apr. 18, 2011 (10 pages).

Written Opinion and International Search Report for PCT/TR2011/000018, mailed May 24, 2011 (10 pages).

Written Opinion and International Search Report for PCT/TR2011/000019, mailed May 11, 2011 (10 pages).

Written Opinion and International Search Report for PCT/TR2011/000021, mailed Dec. 28, 2011 (8 pages).

Written Opinion and International Search Report for PCT/TR2011/000022, mailed Dec. 28, 2011 (9 pages).

Written Opinion and International Search Report for PCT/TR2011/000023, mailed May 24, 2011 (12 pages).

\* cited by examiner

DRY POWDER FORMULATION CONTAINING TIOTROPIUM FOR INHALATION

CROSS-REFERENCE TO RELATED APPLICATIONS

This application is a continuation-in-part of PCT/TR2010/000185, PCT/TR2010/000187, PCT/TR2010/000188, and PCT/TR2010/000189, filed Sep. 22, 2010, PCT/TR2010/000251, filed Dec. 20, 2010, and PCT/TR2011/000011, PCT/TR2011/000012, PCT/TR2011/000014, PCT/TR2011/000015, PCT/TR2011/000018, PCT/TR2011/000019, PCT/TR2011/000021, PCT/TR2011/000022, and PCT/TR2011/000023, filed Jan. 28, 2011, which are incorporated herein by reference in their entireties. This application is entitled to and claims priority benefits to application Serial Numbers TR2009/09788, TR2009/09789, TR2009/09790, TR2009/09792, and TR2009/09793, filed Dec. 25, 2009, TR2010/00619, TR2010/00620, TR2010/00621, TR2010/00622, TR2010/00623, and TR2010/00624, filed Jan. 28, 2010, TR2010/00679, TR2010/00680, and TR2010/00681, filed Jan. 29, 2010, and TR/2010/00729, TR/2010/00730, TR/2010/00731, and TR/2010/00732, filed Feb. 2, 2010.

BACKGROUND OF THE INVENTION

Tiotropium (Formula I) is an anticholinergic agent with the chemical name $(1\alpha,2\beta,4\beta,7\beta)$-7-[(hydroxidi-2-thienylacetyl)oxy]-9,9-dimethyl-3-oxa-9-azoniatricyclo$[3.3.1.0^{2,4}]$nonane.

(Formula I)

Tiotropium was described in European patent application numbered EP0418716 for the first time. Processes to prepare tiotropium; pharmaceutical compositions containing tiotropium; long-acting, strong anticholinergic activity of tiotropium and its use in the treatment of respiratory disorders were disclosed in that patent document.

Tiotropium, especially tiotropium bromide, is a highly effective anticholinergic with the ease of use it provides as it requires once daily use in the treatment of respiratory disorders, particularly asthma and COPD.

Tiotropium antagonises the effect of acetylcholine by blocking cholinergic muscarinic receptors. Tiotropium is separated from M1 and M3 receptors that cause bronchoconstruction slowly while it is separated from M2 receptors that inhibit the release of acetylcholine from cholinergic nerve endings rapidly.

It is possible that the pharmaceutical formulation containing tiotropium is in the form of solution, aerosol or dry powder that are administered via inhalation route. In addition, dry powder formulations are given great importance because of several reasons such as the ease of use that the designed inhalation devices provide and the application possibilities providing long-term stability that they allow.

The delivery of the active agents, such as tiotropium, that shows high efficiency even at low doses to the lungs in efficient and sufficient amounts so as to obtain the desired effects is of great importance because it is considerably difficult to deliver sufficient amounts of these active substances including tiotropium to the lungs as they are very small in amount per dose required for the treatment. Therefore, said active substances have to be diluted with inactive excipients.

The dry powder formulation should have good flow properties in order to provide accurate dosing while the dry powder formulation is being packed and divided into the reservoirs of multi-dose inhalation devices which contain more than one dose or blister cavities of blister packages each of which contains one dose or capsules which contain one dose, after the preparation of the dry powder formulation containing active substance and excipient.

In addition to this, the fact that the dry powder formulation has good flow properties substantially affects the discharge capacity and discharge characteristics of said dry powder formulation during the inhalation from the capsule, blister or reservoir.

The amount of the excipient used in the preparation of the dry powder formulation is much more than the amount of the active substance used. Since the proportion of the excipient to the active agent in the dry powder formulation is high, the excipient choice is effective on the properties of the dry powder formulation to a considerable extent. Thus, the particle size which is one of the physical properties of the excipient directly affects the flow properties of the dry powder formulation. The desired efficiency would be gained as the active agent is sufficiently transmitted to the lungs in dry powder formulations that have good flow properties.

In order to describe the active substance used for the preparation of the dry powder formulation as inhalable, the particles of the active substance have to be conveyed deep into the branches of the lungs with inhaled air. Thus, the required particle size is in the range of 1 and 10 μm, preferably less than 6 μm.

The aim of the present invention is to prepare a dry powder formulation which contains tiotropium; allows highly accurate dosing that provides the inhalable active substance to be in equal and accurate amounts in each blister, capsule or reservoir during the manufacture process; and is inhaled from the capsule, blister or the reservoir in which it is kept with high discharge capacity.

The patent application WO 2004047796 is related to a preparation in dry powder form containing tiotropium and excipients.

The patent application WO 02080884 is related to a preparation in dry powder form containing at least one micronized or spray dried water-soluble active agent, excipient and fatty acid or alcohol derivative or a poloxamer.

The U.S. Pat. No. 5,478,578 is related to a preparation in dry powder form containing micronized active substance and physiologically acceptable excipient.

The dry powder formulation containing tiotropium that has a therapeutic efficacy even at very low doses has to be blended homogeneously in order to provide highly accurate dosing. It has a great significance for the delivery of tiotropiumin in the dry powder formulation to the lungs in efficient and sufficient amounts that the components constituting the dry powder formulation have uniform dispersion properties besides being blended homogeneously.

In accordance with this, a further aim of the present invention is to provide a dry powder formulation containing tiotropium, having uniform dispersion properties and homogeneously blended components. Therefore, the delivery of the inhalable active substance amount contained in the dry powder formulation is achieved with minimum possible variability in every inhalation.

SUMMARY OF THE INVENTION

The present application features the inventions disclosed in PCT/TR2010/000185, PCT/TR2010/000187, PCT/TR2010/000188, and PCT/TR2010/000189, filed Sep. 22, 2010, PCT/TR2010/000251, filed Dec. 20, 2010, and PCT/TR2011/000011, PCT/TR2011/000012, PCT/TR2011/000014, PCT/TR2011/000015, PCT/TR2011/000018, PCT/TR2011/000019, PCT/TR2011/000021, PCT/TR2011/000022, and PCT/TR2011/000023, filed Jan. 28, 2011, the claims of which are hereby incorporated by reference in their entireties.

DETAILED DESCRIPTION OF THE INVENTION

It has been surprisingly found that the objectives mentioned above are achieved by means of the dry powder formulation described hereinbelow which is suitable to be administered via inhalation route.

In accordance with this, the present invention is related to a dry powder formulation containing 0.001% to 1% of tiotropium by weight blended with a physiologically acceptable excipient which is a blend of:

a) a finer excipient with an average particle size of 7 to 10 µm, b) a coarser excipient with an average particle size of 35 to 45 µm, and c) a much coarser excipient with an average particle size of 85 to 95 µm.

The dry powder formulation in accordance with the present invention is characterized in that said excipient consists of three fractions of excipient, each of which have an average particle size range different in other portions, and the amount of the finer excipient is in the range of 17% and 20% of the total amount of the dry powder formulation by weight.

Additionally, according to the present invention, the amount of the coarser excipient contained in the dry powder formulation is in the range of 50% to 70%, preferably in the range of 57% to 64% of the total amount of the dry powder formulation by weight and the amount of the much coarser excipient contained in the dry powder formulation is in the range of 19% to 30%, preferably in the range of 20% to 25% of the total amount of the dry powder formulation by weight.

In accordance with the present invention, the dry powder formulation which contains tiotropium between 0.01% and 0.96%, preferably between 0.01% and 0.85% by weight.

What is meant with the term tiotropium is free ammonium cation. Chloride, bromide, iodide, methanesulphonate, paratoluenesulphonate or methyl sulphate may be used as a counter-ion. However, bromide is preferred among these anions. Accordingly, the present invention is related to the dry powder formulation which contains preferably between 0.01 and 0.82% more preferably between 0.01 and 0.75% of tiotropium bromide by weight.

In addition, the tiotropium bromide contained in the dry powder formulation is preferably tiotropium bromide anhydrous. Thus, the dry powder formulation in accordance with the present invention contains 0.01 to 0.80%, preferably 0.01 to 0.72% of tiotropium bromide anhydrous by weight.

According to the present invention, the excipient contained in the dry powder formulation is characterised by the blend of a finer excipient with an average particle size of 7 to 10 µm, preferably 7 to 9 µm; a coarser excipient with an average particle size of 35 to 45 µm, preferably 37 to 43 µm; and a much coarser excipient with an average particle size of 85 to 95 µm, preferably 87 to 93. The dry powder formulation wherein the amount of the finer excipient is in the range of 17% to 20%, preferably 17% to 19% of the total amount of the dry powder formulation is prepared.

The term "average particle size" refers to the particles wherein 50% of the particles (by volume) have particle sizes less than or equal to the mentioned value. Average particle size value is measured with laser diffractometer.

According to the present invention, physiologically acceptable excipients contained in the dry powder formulation are selected from a group comprising monosaccharides (e.g. glucose, arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or the blends thereof.

According to the present invention, the fine, the coarser and the much coarser excipient fractions may be comprised of identical or different chemical substances. All of the excipient fractions are preferably comprised of identical chemical substances in the dry powder formulation which is subject to the present invention.

According to the present invention, preferably mono or disaccharides are used as excipient in the preparation of the dry powder formulation while lactose is particularly preferred and lactose anhydrous is particularly preferred.

The dry powder formulations prepared in accordance with the present invention may be administered via single or multi-dose inhalers. Accordingly, the dry powder formulation may be inhaled from a multiple dose reservoir according to the U.S. Pat. No. 4,570,630A, from a single dose capsule according to the patent application WO 94/28958 or from a single dose blister according to the patent application US Pat. No. 2002/053344A.

If the dry powder formulation in accordance with the present invention is inhaled from a capsule, which is one of the inhalation methods mentioned above, each capsule is filled with 2 to 10 mg, preferably 3 to 8 mg of the dry powder formulation. Besides, the dry powder formulation which is stored in a capsule with a filling amount of 2 to 10 mg contains between 2.2 and 65 µg, preferably between 3 and 40 µg, most preferably between 4 and 25 µg of tiotropium per capsule. Furthermore, the dry powder formulation which is stored in a capsule with a filling amount of 3 and 8 mg contains between 3.3 and 52 µg, preferably between 4 and 40 µg, most preferably between 5 and 25 µg of tiotropium per capsule.

However, in the case that tiotropium bromide anhydrous is used to prepare the dry powder formulation, the dry powder formulation which is stored in a capsule with a filling amount of 2 and 10 mg contains between 4.6 and 56 µg, preferably between 5 and 35 µg, most preferably between 6 and 25 µg of tiotropium bromide anhydrous per capsule. In addition, the dry powder formulation which is stored in a capsule with a filling amount of 3 to 8 mg contains between 4.6 and 56 µg, preferably between 5 and 35 µg, most preferably between 6 and 25 µg of tiotropium bromide anhydrous per capsule.

In the case that the dry powder formulation of the present invention which is comprised of three excipient fractions with different average particle sizes is stored in a capsule with a filling amount of 2 to 10 mg, it contains between 0.34 and 2 mg, preferably between 0.51 and 1.6 mg of the finer excipient.

If the dry powder formulation in accordance with the present invention is inhaled from a blister, which is one of the inhalation methods mentioned above, each blister is filled with 10 to 21 mg, preferably 12 to 18 mg of the dry powder formulation. In addition, the dry powder formulation which is stored in a blister with a filling amount of 10 to 21 mg contains between 2.9 and 50.9 μg, preferably between 3.2 and 48 μg, most preferably between 4.4 and 42 μg of tiotropium per blister. Furthermore, the dry powder formulation which is stored in a capsule with a filling amount of 12 and 18 mg contains between 3.6 and 32.4 μg, preferably between 4.2 and 28 μg, most preferably between 5 and 24 μg of tiotropium per blister.

However, in the case that tiotropium bromide anhydrous is used to prepare the dry powder formulation according to the present invention, the dry powder formulation which is stored in a blister with a filling amount of 10 and 21 mg contains between 3.6 and 54 μg, preferably between 4 and 36 μg, most preferably between 6 and 28 μg of tiotropium bromide anhydrous per blister. In addition, the dry powder formulation which is stored in a blister with a filling amount of 12 to 18 mg contains between 4.6 and 52 μg, preferably between 5 and 35 μg, most preferably between 6 and 25 μg of tiotropium bromide anhydrous per blister.

In the case that the dry powder formulation in accordance with the present invention which is comprised of three excipient fractions with different average particle sizes is stored in a blister with a filling amount of 10 to 21 mg, it contains between 1.7 to 4.2 mg, preferably between 2.1 and 3.6 mg of the finer excipient.

The dry powder formulation in accordance with the present invention is prepared as described hereinbelow.

According to the present invention, tiotropium, preferably tiotropium bromide anhydrous, to be used as an active agent in the preparation of the dry powder formulation, the finer excipient fraction, the coarser excipient fraction and the much coarser excipient fraction are weighted in accordance with the abovementioned proportions.

According to the present invention, the components used in the preparation of the dry powder formulation are included in the proportions described before.

The dry powder formulation in accordance with the present invention is prepared by blending the components properly and in the abovementioned amounts. Accordingly, each of tiotropium, preferably tiotropium bromide anhydrous, and the finer excipient fraction is sieved through a sieve with a suitable pore size at least once. Each of said components is sieved preferably layer by layer through said sieve at least once. Then, they are blended in a mixing container to obtain premix-A.

Afterwards, each of the coarser excipient fraction and premix-A is sieved through a sieve with a suitable pore size at least once. Each of said components is sieved preferably layer by layer through the mentioned sieve at least once. Then, they are blended in a separate mixing container to obtain premix-B. Finally, after premix B is sieved preferably through a sieve with a suitable pore size at least once, it is fed into a mixing container in which the much coarser excipient fraction that was sieved at least once through a sieve with a suitable pore size is placed. Each of premix-B and the much coarser excipient fraction is sieved preferably layer by layer from the mentioned sieve at least once before being blended.

One aspect of the present invention is related to a dry powder formulation containing tiotropium that can be prepared by the method described above.

Within the scope of the present invention, the term "active substance" refers to tiotropium. The term tiotropium also includes its pharmaceutically acceptable solvates, hydrates, organic salts, inorganic salts, esters, free base, polymorphs, crystalline forms and amorphous forms and combinations thereof. The salt of the tiotropium corresponds to the combination of tiotropium, which is free ammonium cation, and an anion as the counter-ion.

What is meant with tiotropium salt used within the scope of the invention is chloride, bromide, iodide, methanesulphonate, para-toluenesulphonate or methyl sulphate as counter ion besides tiotropium. Within the scope of the present invention, tiotropium bromide is preferred among all of the defined salts of tiotropium. Within the scope of the present invention, "tiotropium bromide" comprises all of the possible crystalline and amorphous modifications of tiotropium bromide. In addition, water-free (anhydrous) forms are preferred among all the crystalline and amorphous forms of tiotropium bromide that the dry powder formulation in accordance with the present invention contains. Accordingly, tiotropium bromide anhydrous is preferably used in the preparation of the dry powder formulation within the scope of the invention.

First of all, tiotropium has to be prepared in a form to be used for pharmaceutical purposes in order to prepare the dry powder formulations in accordance with the present invention. To this end, tiotropium bromide which is produced as disclosed in the patent application EP 418 716 A1 is processed to obtain tiotropium bromide anhydrous and it is micronized to attain the appropriate particle sizes for the present invention.

Three physiologically acceptable excipient fractions with different average particle sizes, which are used to prepare the dry powder formulation in accordance with the present invention, may be comprised of chemically identical or different substances. According to the present invention, physiologically acceptable excipients contained in the dry powder formulation can be selected from a group comprising monosaccharides (e.g. glucose, arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or the mixtures thereof. However, all the excipient fractions used in the preparation of the dry powder formulation in accordance with the present invention consists of preferably lactose, most preferably lactose anhydrous. Said excipient fractions, which consist of most preferably lactose anhydrous, are subjected to micronization to obtain particles in the average sizes mentioned before.

The dry powder formulation, which is prepared in accordance with the invention, is administered via single or multi-dose inhalers. Therefore, the dry powder formulation in accordance with the present invention is inhaled from a multi dose reservoir, a single dose capsule or a single dose blister.

According to the present invention, in the cases that the dry powder formulation is stored in a reservoir, more than one dose of the dry powder formulation is placed in the reservoir and one dose of the dry powder formulation is inhaled by the patient when the inhaler is actuated.

In the case that the dry powder formulation in accordance with the present invention is carried in a capsule, the additional components within the inhaler provide the capsule to be opened or pierced in every actuation of the inhaler so as to make the dry powder formulation ready for inhalation and then the dry powder formulation becomes ready for inhalation. After the inhalation, the empty capsule is removed from the inhaler and a new capsule is placed into the inhaler immediately before the following inhalation.

If a capsule is used to store the dry powder formulation in accordance with the present invention, the capsule volume is in the range of 0.1 to 0.52 ml, preferably in the range of 0.1 to 0.45 ml, more preferably in the range of 0.15 to 0.42 ml.

The humidity rate of the capsule pack which contains the dry powder formulation in accordance with the present invention is in the range of 10-20%, preferably in the range of 15-20% by weight. In the case that the capsules having the specified properties are used, the dry powder formulation in the capsule is protected from external effects and the moisture that may result from the structure of the capsule itself is prevented. In this way, agglomeration of the dry powder is prevented and it is possible to administer the dry powder to the patient in the most effective way.

The capsule that contains the dry powder formulation in accordance with the present invention can be made of a material selected from a group comprising gelatine, chitosan, starch and/or starch derivatives or synthetic polymers. The capsule consists of intertwining top and bottom compartments. In said capsules, the top and the bottom compartments can be made of the same or different materials.

According to this, in the case that the capsule containing the dry powder formulation is made of cellulose or its derivatives, the capsule material can be selected from, but not limited to, a group comprising hydroxypropyl cellulose, hydroxypropylmethyl cellulose, methyl cellulose, hydroxymethyl cellulose, hydroxyethyl cellulose.

In the case that the capsule which contains the dry powder formulation in accordance with the present invention is synthetic polymer, the capsule material can be selected from, but not limited to, a group comprising; polyethylene, polyester, polytheleneteraphtalate, polycarbonate or polypropylene.

In the case that the capsule which contains the dry powder formulation in accordance with the present invention is gelatine, additional agents such as polyethylene glycol at different molecular weights, sorbitol, glycerol, propylene glycol, polyethylene oxide-polypropylene oxide block copolymers and/or other polyalcohols or polyethers can be added in the gelatine.

The capsule with the specified volume that is used to store the dry powder formulation in accordance with the present invention is filled up to 0.01% to 25% of its total volume, preferably 0.1 to 20% of its total volume, more preferably 0.5 to 17% of its total volume.

The capsule pack that contains the dry powder formulation in accordance with the present invention can be in any color or shape as long as it has the properties described above.

According to the present invention, the dry powder formulation can also be carried in blisters besides reservoirs and capsules. Blister package consists of blisters, each of which is placed in a particular order and contains one dose of the dry powder formulation. The blister package can be opened by being pierced or peeled depending on the inhaler design. However, the blister package which contains the dry powder formulation in accordance with the present invention is preferably a peelable blister package. Each time the inhaler is actuated, a blister containing the dry powder formulation is opened by being pierced or peeled and the dry powder formulation becomes ready for the inhalation.

The blisters that are placed on the blister package in a particular order provide to carry and store the dry powder formulation in accordance with the present invention. Each blister contains 10 mg to 21 mg, preferably 12 mg to 18 mg of the dry powder formulation and has a cavity volume in the range of 20 to 30 mm$^3$ preferably in the range of 21 to 25 mm$^3$, most preferably in the range of 22-23 mm$^3$.

Each blister cavity which is used to carry and store the dry powder formulation in accordance with the present invention and has the specified volume is filled up to 25-100%, preferably up to 70-100%, most preferably up to 90-100% of its total volume.

The peelable blister package wherein the blisters having the mentioned properties are placed side by side consists of a lid sheet and a base sheet which are closed very tightly by any suitable method to provide impermeability.

The lid sheet and the base sheet of the peelable blister package which contains the dry powder formulation in accordance with the present invention consist of many layers such as polymeric layer, aluminum foil and optionally Aclar® fluoropolimer film.

Aclar® fluoropolymer film is a polymeric film which is used for production of the blister package and provides high moisture protection. This chemically inert film does not cause any change in taste of the formulation when it is in contact with the dry powder formulation. It easily forms a layered structure with the other polymeric layers which are composed of various polymers. It is appropriate to be transacted with heat.

In order to decrease the gas and moisture permeability of the layer, preferably desiccant agents are added to the polymeric layers to preserve the stability of the dry powder formulation stored in blisters that are arranged in an order on the blister package. Silica gel, zeolite, alumina, bauxite, anhydrous calcium sulfate, activated carbon and clay which have the property of water absorption can be given as examples to desiccant agents.

As it is common to use aluminum in lid and base sheets of high protection peelable blister packages, aluminum can be used both in the lid and the base sheets of the blister package of the present invention in order to provide high moisture and gas protection. The thickness of the aluminum foil that is used in the lid and the base sheets of the blister package is chosen to be in the range of 10 to 40 µm, preferably of 15 to 30 µm.

The polymeric layers in the lid and the base sheets of the peelable blister package in accordance with the present invention are made from the same or different polymers. The thickness of these polymeric layers varies according to the type of the polymeric substance used and its properties. Therefore, the thickness of the polymeric layer varies in the range of 15-60 µm, preferably of 20-35 µm depending on the type of the polymer used.

The inside layer of the blister cavity of the said blister package which is in contact with the dry powder formulation is a polymeric layer because of the fact that some of the dry powder formulation sticks onto the inside layer of the blister cavity due to the porous structure of aluminum foil and electrostatic forces, and hence causes uncontrolled dosing.

According to the present invention, the polymers used to form the polymeric layers are preferably selected from a group comprising thermo-plastic polymers such as polyethylene, polypropylene, polystyrene, polyolefin, polyamide, polyvinyl chloride, polyurethane or other synthetic polymers.

In addition, the blisters which constitute the blister package in accordance with the present invention can be in any shape as long as they have the properties described above.

After the dry powder formulation is prepared through the above mentioned methods, it is filled into capsules and blisters in the amounts stated before. In order to make the present invention clearer, the components contained in the blisters and the capsules and the amounts of these components are illustrated with, but not restricted to, the examples below

A: EXAMPLES ON THE CAPSULE CONTENT

Example 1

| Content of the formulation | Amount |
|---|---|
| Tiotropium bromide anhydrous | 0.02 mg |
| Finer lactose anhydrous (8 μm) | 0.78 mg |
| Coarser lactose anhydrous (40 μm) | 2.66 mg |
| Much coarser lactose anhydrous (90 μm) | 1.04 mg |
| Total | 4.5 mg |

Example 2

| Content of the formulation | Amount |
|---|---|
| Tiotropium bromide anhydrous | 0.02 mg |
| Finer lactose anhydrous (8 μm) | 0.98 mg |
| Coarser lactose anhydrous (40 μm) | 3.35 mg |
| Much coarser lactose anhydrous (90 μm) | 1.15 mg |
| Total | 5.5 mg |

Example 3

| Content of the formulation | Amount |
|---|---|
| Tiotropium bromide anhydrous | 0.02 mg |
| Finer lactose anhydrous (7 μm) | 0.83 mg |
| Coarser lactose anhydrous (35 μm) | 2.76 mg |
| Much coarser lactose anhydrous (85 μm) | 0.89 mg |
| Total | 4.5 mg |

Example 4

| Content of the formulation | Amount |
|---|---|
| Tiotropium bromide anhydrous | 0.02 mg |
| Finer lactose anhydrous (8 μm) | 0.96 mg |
| Coarser lactose anhydrous (40 μm) | 3.27 mg |
| Much coarser lactose anhydrous (90 μm) | 1.25 mg |
| Total | 5.5 mg |

Example 5

| Content of the formulation | Amount |
|---|---|
| Tiotropium bromide anhydrous | 0.02 mg |
| Finer lactose anhydrous (9 μm) | 0.81 mg |
| Coarser lactose anhydrous (42 μm) | 2.77 mg |
| Much coarser lactose anhydrous (87 μm) | 0.9 mg |
| Total | 4.5 mg |

Example 6

| Content of the formulation | Amount |
|---|---|
| Tiotropium bromide anhydrous | 0.02 mg |
| Finer lactose anhydrous (8 μm) | 0.79 mg |
| Coarser lactose anhydrous (38 μm) | 2.77 mg |
| Much coarser lactose anhydrous (86 μm) | 0.92 mg |
| Total | 4.5 mg |

Example 7

| Content of the formulation | Amount |
|---|---|
| Tiotropium bromide anhydrous | 0.02 mg |
| Finer lactose anhydrous (10 μm) | 0.82 mg |
| Coarser lactose anhydrous (43 μm) | 2.68 mg |
| Much coarser lactose anhydrous (89 μm) | 0.98 mg |
| Total | 4.5 mg |

B: EXAMPLES ON THE BLISTER CONTENT

Example 8

| Content of the formulation | Amount |
|---|---|
| Tiotropium bromide anhydrous | 0.02 mg |
| Finer lactose anhydrous (9 μm) | 3.24 mg |
| Coarser lactose anhydrous (42 μm) | 9.86 mg |
| Much coarser lactose anhydrous (88 μm) | 3.88 mg |
| Total | 17.0 mg |

Example 9

| Content of the formulation | Amount |
|---|---|
| Tiotropium bromide anhydrous | 0.02 mg |
| Finer lactose anhydrous (8 μm) | 2.96 mg |
| Coarser lactose anhydrous (43 μm) | 9.29 mg |
| Much coarser lactose anhydrous (91 μm) | 2.73 mg |
| Total | 15 mg |

Example 10

| Content of the formulation | Amount |
|---|---|
| Tiotropium bromide anhydrous | 0.02 mg |
| Finer lactose anhydrous (9 μm) | 3.15 mg |
| Coarser lactose anhydrous (42 μm) | 10.07 mg |
| Much coarser lactose anhydrous (87 μm) | 3.76 mg |
| Total | 17 mg |

Example 11

| Content of the formulation | Amount |
|---|---|
| Tiotropium bromide anhydrous | 0.02 mg |
| Finer lactose anhydrous (7 μm) | 2.85 mg |
| Coarser lactose anhydrous (38 μm) | 8.58 mg |
| Much coarser lactose anhydrous (86 μm) | 3.55 mg |
| Total | 15 mg |

Example 12

| Content of the formulation | Amount |
|---|---|
| Tiotropium bromide anhydrous | 0.02 mg |
| Finer lactose anhydrous (8 μm) | 3.2 mg |
| Coarser lactose anhydrous (43 μm) | 10.35 mg |
| Much coarser lactose anhydrous (91 μm) | 3.43 mg |
| Total | 17 mg |

Example 13

| Content of the formulation | Amount |
|---|---|
| Tiotropium bromide anhydrous | 0.02 mg |
| Finer lactose anhydrous (10 μm) | 3.25 mg |
| Coarser lactose anhydrous (45 μm) | 10.27 mg |
| Much coarser lactose anhydrous (92 μm) | 3.46 mg |
| Total | 17.0 mg |

Example 14

| Content of the formulation | Amount |
|---|---|
| Tiotropium bromide anhydrous | 0.02 mg |
| Finer lactose anhydrous (7 μm) | 3.35 mg |
| Coarser lactose anhydrous (38 μm) | 9.98 mg |
| Much coarser lactose anhydrous (86 μm) | 3.65 mg |
| Total | 17 mg |

The dry powder formulation in accordance with the present invention can be used in treatment of many respiratory diseases especially asthma, chronic obstructive pulmonary disorder (COPD) and allergic rhinitis. Accordingly, the respiratory diseases include, but not restricted to, allergic or non-allergic asthma in various phases, acute lung injury (ALI), acute respiratory distress syndrome (ARDS), exacerbation of airways hyperactivity, bronchiectasis, chronic obstructive pulmonary, airways or lung diseases (COPD, COAD or COLD) including emphysema and chronic bronchitis, pneumoconiosis, aluminosis, anthracosis, asbestosis, chalicosis, ptilosis, siderosis, silicosis, tabacosis and byssinosis. The treatment of said diseases may be prophylactic or symptomatic. In addition to this, the dry powder formulation in accordance with the present invention is used especially for the symptomatic treatment of asthma, allergic rhinitis and COPD.

What is claimed is:

1. A dry powder formulation containing 0.001% to 1% of tiotropium by weight as blended with a physiologically acceptable excipient characterized in that said excipient is comprised of the blend of a finer excipient with an average particle size of 7 to 10 μm, a coarser excipient with an average particle size of 35 to 45 μm, and a much coarser excipient with an average particle size of 85 to 95 μm and the amount of the finer excipient is in the range of 17% to 20% by weight of the total amount of the dry powder formulation, wherein the amount of the coarser excipient is in the range of 50% to 70% by weight of the total amount of the dry powder formulation.

2. The dry powder formulation of claim 1, wherein said dry powder formulation contains pharmaceutically acceptable solvates, hydrates, organic salts, inorganic salts, esters, free base, polymorphs, crystalline forms and amorphous forms of tiotropium and their mixtures.

3. The dry powder formulation of claim 1, wherein tiotropium is present in a form that is tiotropium bromide.

4. The dry powder formulation of claim 1, wherein said dry powder formulation contains between 0.01% and 0.96% of tiotropium by weight.

5. The dry powder formulation according to claim 1, wherein said dry powder formulation contains between 0.01 and 0.80% of tiotropium bromide anhydrous by weight.

6. The dry powder formulation according to claim 1, wherein said excipient consists of the blend of the finer excipient with an average particle size of 7 to 9 μm, the coarser excipient with an average particle size of 37 to 43 μm, and the much coarser excipient with an average particle size of 87 to 93 μm.

7. The dry powder formulation according to claim 1, wherein the amount of the finer excipient is in the range of 17% to 19% of the total amount of the dry powder formulation.

8. The dry powder formulation of claim 1, wherein the amount of the coarser excipient is in the range of 57% to 64% by weight of the total amount of the dry powder formulation.

9. The dry powder formulation according to claim 1, wherein the particle size of tiotropium is in the range of 0.1 μm to 10 μm.

10. The dry powder formulation according to claim 1, wherein all of the excipient fractions contained by the physiologically acceptable excipient are comprised of chemically different substances.

11. The dry powder formulation according to claim 1, wherein all of the excipient fractions contained by the physiologically acceptable excipient are comprised of chemically identical substances.

12. The dry powder formulation according to claim 1, wherein the physiologically acceptable excipient is selected from the group consisting of monosaccharides, disaccharides, oligo- and polysaccharides, polyalcohols, salts or mixtures of these excipients with one another.

13. The dry powder formulation according to claim 1, wherein the physiologically acceptable excipient is selected from disaccharides.

14. The dry powder formulation according to claim 1, wherein the physiologically acceptable excipient is lactose.

15. The dry powder formulation according to claim 1, wherein said dry powder formulation is used in the preparation of a capsule which is suitable for inhalation.

16. The dry powder formulation according to claim 1, wherein said dry powder formulation is stored in a capsule with a filling amount of 2 mg to 10 mg of the dry powder formulation.

17. The dry powder formulation according to claim 1, wherein said dry powder formulation is stored in a capsule which has a volume of 0.1 to 0.52 ml.

18. The dry powder formulation according to claim 1, wherein said dry powder formulation is stored in a capsule filled up to 0.01% to 25% of its total volume.

19. The dry powder formulation according to claim 1, wherein said dry powder formulation is used in the preparation of a blister package suitable for inhalation.

20. The dry powder formulation according to claim 1, wherein said dry powder formulation is stored in a blister package in which each of the blisters is filled with 10 mg to 21 mg of the dry powder formulation.

21. The dry powder formulation according to claim 1, wherein said dry powder formulation is stored in a blister package in which each of the blisters has a cavity volume in the range of 20 to 30 mm$^3$.

22. The dry powder formulation according to claim 1, wherein said dry powder formulation is stored in a blister package in which each of the blisters is filled up to 25-100% of the its total volume.

23. The dry powder formulation according to claim 1, wherein said dry powder formulation is used in the treatment of respiratory diseases.

24. The dry powder formulation according to claim 23, wherein said respiratory disease is asthma or chronic obstructive pulmonary disorder.

25. A dry powder formulation containing 0.001% to 1% of tiotropium by weight as blended with a physiologically acceptable excipient characterized in that said excipient is comprised of:
    the blend of a finer excipient with an average particle size of 7 to 10 μm,
    a coarser excipient with an average particle size of 35 to 45 μm, and
    a much coarser excipient with an average particle size of 85 to 95 μm,
    wherein the amount of the finer excipient is in the range of 17% to 20% by weight of the total amount of the dry powder formulation and wherein the amount of the much coarser excipient is in the range of 19% to 30% by weight of the total amount of the dry powder formulation.

26. The dry powder formulation according to claim 1, wherein said dry powder formulation contains chloride, bromide, iodide, methanesulphonate, para-toluenesulphonate, or methyl sulphate salt of tiotropium as active substance.

27. The dry powder formulation according to claim 1, wherein tiotropium is present in the form that is tiotropium bromide anhydrous.

28. The dry powder formulation according to claim 1, wherein said dry powder formulation contains between 0.01% and 0.85% of tiotropium by weight.

29. The dry powder formulation according to claim 1, wherein said dry powder formulation contains between 0.01 and 0.72% of tiotropium bromide anhydrous by weight.

30. The dry powder formulation according to claim 1, wherein the particle size of tiotropium is in the range of 1 μm to 6 μm.

31. The dry powder formulation of claim 1, wherein the physiologically acceptable excipient is lactose anhydrous.

32. The dry powder formulation according to claim 1, wherein said dry powder formulation is stored in a capsule with a filling amount of 3 mg to 8 mg of the dry powder formulation.

33. The dry powder formulation according to claim 1, wherein said dry powder formulation is stored in a capsule which has a volume of 0.1 to 0.45 ml.

34. The dry powder formulation according to claim 1, wherein said dry powder formulation is stored in a capsule which has a volume of 0.15 to 0.42 ml.

35. The dry powder formulation according to claim 1, wherein said dry powder formulation is stored in a blister package in which each of the blisters is filled with 12 mg to 18 mg of the dry powder formulation.

36. A method for preparing the dry powder formulation according to claim 1, characterized in that said method comprises the steps of:
    (a) blending tiotropium with the finer excipient fraction to obtain Premix A,
    (b) blending Premix A with the coarser excipient fraction to obtain Premix B, and
    (c) blending Premix B with the much coarser excipient fraction.

37. The dry powder formulation according to claim 25, wherein the amount of the much coarser excipient is in the range of 20% to 25% by weight of the total amount of the dry powder formulation.

* * * * *